United States Patent [19]
Dreisbach

[11] Patent Number: 6,153,414
[45] Date of Patent: Nov. 28, 2000

[54] METHOD FOR RACEMIC BIOCHEMICAL RESOLUTION OF CIS-AND TRANS-PYPROLOPIPERIDINE

[75] Inventor: Claus Dreisbach, Köln, Germany

[73] Assignee: Bayer Aktiengesellschaft, Leverkusen, Germany

[21] Appl. No.: 09/485,083

[22] PCT Filed: Aug. 1, 1998

[86] PCT No.: PCT/EP98/04820

§ 371 Date: Feb. 3, 2000

§ 102(e) Date: Feb. 3, 2000

[87] PCT Pub. No.: WO99/09200

PCT Pub. Date: Feb. 25, 1999

[30] Foreign Application Priority Data

Aug. 14, 1997 [DE] Germany ............................ 197 35 198

[51] Int. Cl.[7] ............................ C12P 41/00; C12P 17/18; C07D 471/04
[52] U.S. Cl. ............................ 435/119; 435/195; 435/227
[58] Field of Search ..................... 435/119, 195, 435/227

[56] References Cited

FOREIGN PATENT DOCUMENTS 0550903 7/1993 European Pat. Off. .
4332738 3/1995 European Pat. Off. .

OTHER PUBLICATIONS

Chimia 48, pp. 570 1994, Reetz et al, Highly Efficient Lipase–Catalyzed Kinetic Resolution of Chiral Amines.
Houben–Weyl, Methoden der organischen Chemie, Methods in Organic Chemistry, 4th edition 1994, H. Henecka: Carbonsäuren.
Advanced Organic Chemistry, 4th edition Reactions Mechanisms, and Structure Jerry March.

Primary Examiner—Herbert J. Lilling
Attorney, Agent, or Firm—Joseph C. Gil; Diderico van Eyl

[57] ABSTRACT

Cis- and trans-pyrrolopiperidines are advantageously separated into their optical isomers when monoacylating by enzymatic process a mixture containing (R,R)- and (S,S)-pyrrolopiperidine or (S,R)- and (R,S)-pyrrolopiperidine, thereby obtaining a mixture (I) containing (R,R)- and (S,S)-6-acyl-pyrrolopiperidine or (S,R)- and (R,S)-6-acyl-pyrrolopiperidine. Said mixture (I) is then again acylated by enzymatic process, thereby obtaining a mixture (II) containing (S,S)-1,6-diacyl- and (R,R)-6-acyl-pyrrolipiperidine or (S,R)-1,6-diacyl- and (R,S)-6-acyl-pyrrolopiperidine; the enzyme and optionally the solvent and the excess acylating agent are separated from the mixture (II), and the rest is treated with aqueous acid, and the (S,S)-1,6-diacyl-pyrrolopiperidine or the (S,R)-1,6-diacyl-pyrrolopiperidine is separated by extraction and the extraction residue is alkalinized, and the (R,R)-6-acyl-pyrrolopiperidine or the (R,S)-6-acyl-pyrrolopiperidine is separated by extraction. From these acylated isomer-free derivatives, the free base can optionally be prepared according to the usual methods for separating acylated groups.

5 Claims, No Drawings

METHOD FOR RACEMIC BIOCHEMICAL RESOLUTION OF CIS-AND TRANS-PYPROLOPIPERIDINE

BACKGROUND OF THE INVENTION

The present invention relates to a method for the racemate resolution of both cis- and trans-pyrrolopiperidine, in which a mixture of acyl derivatives of the cis- or trans-pyrrolopiperidine is prepared in the presence of enzymes, and this mixture, following treatment with acids and base, is separated off and by extraction.

Enantiomerically pure pyrrolopiperidines are important intermediates for the preparation of quinolone and naphthyridine derivatives having antibacterial effectiveness (see EP-A 550 903). This EP-A also describes a process for the preparation of enantiomerically pure cis-pyrrolopiperidines in which the racemate resolution is carried out by means of crystallization on 6-benzyl derivatives of the pyrrolopiperidine. A disadvantage in this connection is the complex crystallization of the enantiomers with enantiomeric auxiliary reagents, the two enantiomers each being crystallized using one ancillary reagent.

In a known process for the preparation of other enantiomerically pure secondary amines, hydrolases are used and the acylation must be carried on using esters in which, in the acid moiety, an electron-rich heteroatom (e.g. fluorine) is present in the vicinity of the carbonyl function (see DE-A 43 32 738). Fluoroacetic acid and its esters are more difficult to obtain than unsubstituted aliphatic carboxylic acids and esters thereof.

In a known process for the racemate resolution of primary arnines, the latter are treated with lipase from Candida antarctica and ethyl acetate, with selective acylation of the (R)-isomer (Chimia 48, 570 (1994)). However, this process is limited to the racemate resolution of primary amines.

We have now found a method for the racemate resolution of cis- and trans-pyrrolopiperidine, which is characterized in that a mixture, which comprises (R,R)- and (S,S)-pyrrolopiperidine or (S,R)- and (R,S)-pyrrolopiperidine, is enzymatically monoacylated to give a mixture (I) which comprises (R,R)- and (S,S)-6-acyl-pyrrolopiperidine or (S,R)- and (R,S)-6-acyl-pyrrolopiperidine, this mixture (I) is enzymatically further acylated to give a mixture (II) which comprises (S,S)-1,6-diacyl- and (R,R)-6-acyl-pyrrolipiperidine or (S,R)-1,6-diacyl- and (R,S)-6-acyl-pyrrolopiperidine, the enzyme and optionally solvent and excess acylating agent are separated off from the mixture (II), and the remainder is treated with aqueous acid, and (S,S)-1,6-diacyl-pyrrolopiperidine or (S,R)-1,6-diacyl-pyrrolopiperidine is separated off by extraction, and the extraction residue is rendered alkaline, and (R,R)-6-acyl-pyrrolopiperidine or (R,S)-6-acyl-pyrrolopiperidine is separated off by extraction.

DESCRIPTION OF THE INVENTION

The process according to the invention can be simplified by the following equation and illustrated using the racemate resolution of cis-pyrrolopiperidine as an example:

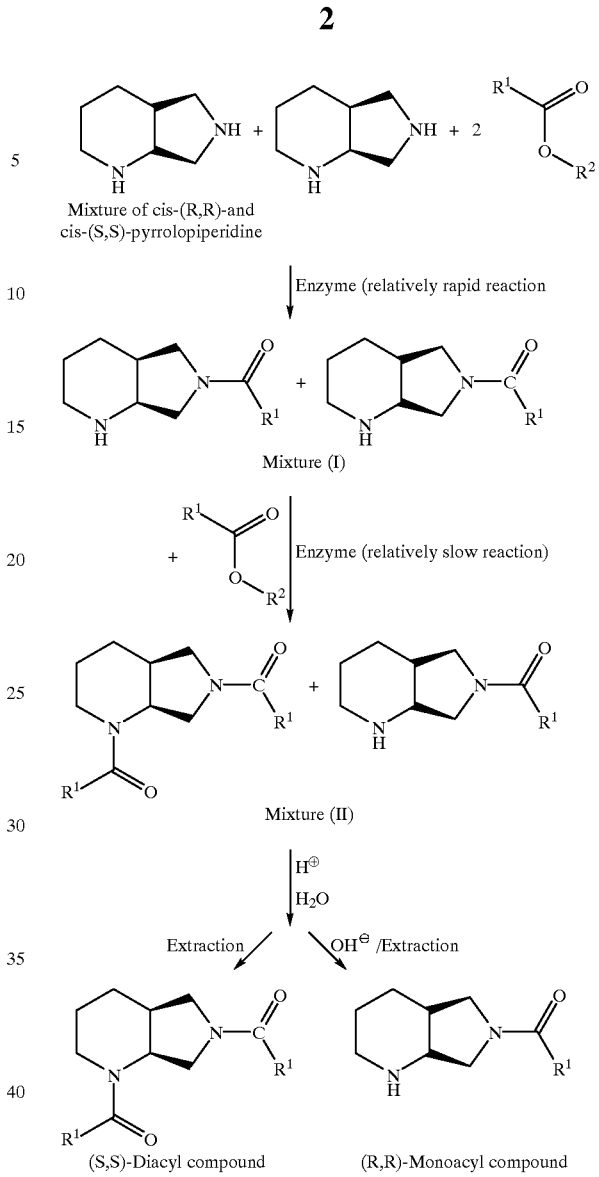

If, instead of cis-pyrrolopiperidine, trans-pyrrolopiperidine is used as starting material, then the method according to the invention proceeds analogously, giving, in the last stage, the (S,R)-diacyl compound and the (R,S)-monoacyl compound.

Generally, the two acylating reactions are carried out as a one-pot reaction and the mixture (I) is not isolated. For this procedure, it is possible to use, for example, from 1 to 35 mol of an acylating agent of the formula (I) per mole of cis- or trans-pyrrolopiperidine. This amount is preferably from 2 to 30 mol.

Suitable reaction temperatures are, for example, those in the range from 10 to 90° C., preferably from 30 to 60° C.

The reaction time for the preparation of the mixture (II) can, for example, be in the range from 200 to 450 hours, preferably from 250 to 350 hours.

Enzymes which can be used are, for example, hydrolases, such as proteases, esterases or lipases. Preference is given to lipases from Pseudomonas or Candida. Particular preference is given to the lipase from Candida antarctica.

The enzymes can be used in native or immobilized form. Immobilization can be carried out, for example, by microencapsulation or by combination with an organic or inorganic carrier material. Suitable carrier materials are, for example, kieselguhr, ion exchangers, zeolites, polysaccharides, polyamides and polystyrene resins, in particular Celite® and Lewatit®. A suitable enzyme is, for example, lipase from Candida antarctica in the form of the commercially available product Novozym® 435 (manufacturer Novo Nordisk).

The amount of enzyme can be varied within wide limits. For example, it is possible to use from 5 to 700% by weight of immobilized enzyme, based on cis- or trans-pyrrolopiperidine used, or a corresponding amount of native enzyme. This amount is preferably from 10 to 600% by weight of immobilized enzyme or the corresponding amount of native enzyme.

Suitable acylating agents are, for example, those of the formula (I)

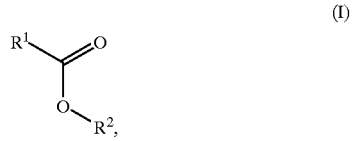

in which $R^1$ and $R^2$ independently of one another are hydrogen or $C_1$–$C_{12}$-alkyl. The alkyl groups can be straight-chain or branched. Preferably, $R^1$ is hydrogen or $C_1$–$C_4$-alkyl and $R^2$ is $C_1$–$C_6$-alkyl. Particular preference is given to using ethyl acetate.

Suitable diluents which are optionally used for the acylating reaction are a wide variety of organic solvents, for example ethers, such as diethyl ether or methyl tert-butyl ether (=MTBE), hydrocarbons, such as toluene, and halogenated hydrocarbons, such as methylene chloride. It is also possible to work without the addition of a particular diluent. It is then expedient to use an excess of the acylating agent of the formula (I).

This method gives a mixture (II), which comprises (S,S)-1,6-diacyl- and (R,R)-6-acyl-pyrrolopiperidine or (S,R)-1,6-diacyl- and (R,S)-6-acyl-pyrrolopiperidine. According to the invention, this mixture is worked up by firstly separating off the enzyme, for example by filtration. The enzyme which has been separated off and optionally washed can be used again in the acylation of cis- or trans-pyrrolopiperidine or for other purposes.

Diluent which may be present and excess acylating agent which may be present can be removed by evaporation, if necessary under reduced pressure.

The reaction mixture which remains following removal of the enzyme and optionally of the diluent and excess acylating agent is then treated with aqueous acid. Suitable acids for this purpose are, for example, 2 to 50% strength by weight aqueous sulphuric, hydrochloric, phosphoric or acetic acid. The amount of aqueous acid can, for example, be measured such that the pH following the addition of acid is 4 or less, preferably 2 or less.

The treatment with aqueous acid can be carried out, for example, at temperatures from 0 to 90° C., preferably from 10 to 50° C.

For the extraction of the mixture present following treatment with the aqueous acid, it is possible to use inert organic solvents which are immiscible or only slightly miscible with water. Examples are chlorinated hydrocarbons, aromatic hydrocarbons and ethers.

Preference is given to toluene, MTBE, diethyl ether, methylene chloride and chloroform. The extraction can be carried out, for example, at from 10 to 50° C.

The extract then comprises the prepared (S,S)-1,6-diacyl-pyrrolopiperidine or (S,R)-1,6-diacyl-pyrrolopiperidine. By removing the extractant, e.g. by evaporation, if necessary at reduced pressure, it is possible to isolate it.

The extraction residue is then rendered alkaline. For this purpose, it is possible to use, for example, alkali metal hydroxides, alkali metal carbonates, alkali metal hydrogencarbonates, calcium hydroxide or ammonia as such or in aqueous solution or suspension. Preference is given to 20 to 50% strength by weight aqueous sodium and potassium hydroxide solution. The amount of alkaline-rendering agent can be measured, for example, such that after its addition the pH is 7.5 or more, preferably 9 or more.

The alkaline mixture then present is likewise extracted. Suitable organic solvents and temperatures for this purpose are those described above. The extract then comprises the prepared (R,R)-6-acyl-pyrrolopiperidine or (R,S)-6-acyl-pyrrolopiperidine. By removing the extractant, e.g. by evaporation, if necessary at reduced pressure, it is possible to isolate it.

In this way it is possible to separate cis- or trans-pyrrolopiperidine into its optical antipodes and to obtain the (S,S)- or (S,R)-isomer in the form of the 1,6-diacyl derivative and the (R,R)- or (R,S)-isomer in the form of the 6-acyl derivative. From these acyl derivatives it is possible, if desired, to obtain the respective pyrrolopiperidine in free form by cleaving off the acyl group(s) by methods known per se (see e.g. Houben-Weyl, Methoden der organischen Chemie [Methods in Organic Chemistry], 4th edition, page 432).

Using the racemate resolution according to the invention, the optical antipodes are generally obtained in optical yields of at least 90% ee and in chemical yields of at least 25%. The optical yields are frequently greater than 95% ee and the chemical yields greater than 35%.

The racemate resolution according to the invention has the additional advantages that it produces both enantiomers in one step and can be carried out using acylating agents which are obtainable at favourable cost.

The present invention further relates to mixtures which comprise (R,R)- and (S,S)-6-acyl-pyrrolopiperidines (such mixtures are also referred to above as mixture (I)). The acyl groups can, for example, be those which have a $C_1$–$C_{12}$-alkyl radical. It is preferably a $C_1$–$C_4$-alkyl radical, in particular a methyl radical. Preferred mixtures are those which comprise (R,R)- and (S,S)-6-acetylpyrrolopiperidine.

Mixtures (I) according to the invention can, in principle, be prepared as described above for the preparation of the mixtures (II), but with the difference that a shorter reaction time is observed for the acylation reaction. The reaction time for the preparation of mixtures (I) can, for example, be from 10 minutes to 20 hours, preferably from 0.5 to 10 hours.

The present invention also relates to (S,S)-1,6-diacyl-pyrrolopiperidines as such. The acyl groups can, for example, be those which have a $C_1$–$C_{12}$-alkyl radical. It is preferably a $C_1$–$C_4$-alkyl radical, in particular a methyl radical. A preferred diacyl-pyrrolopiperidine of this type is (S,S)-1,6-diacetyl-pyrrolopiperidine.

The invention is further described in the following illustrative examples in which all parts and percentages are by weight unless otherwise indicated.

The present invention relates finally also to (R,R)-6-acyl-pyrrolopiperidines and (R,R)-1,6-diacyl-pyrrolopiperidines.

EXAMPLES

The enantiomer excesses were determined by GC over cyclodextrin columns, and the configuration was determined by comparison with authentically synthesized pyrrolopiperidines.

Example 1

10 g of racemic cis-pyrrolopiperidine were dissolved in 250 ml of ethyl acetate, and 60 g of Novocym® 435 were added. The mixture was then stirred slowly for 14 days at 40° C. The enzyme was filtered off, and the filter cake was washed with ethyl acetate. The combined organic solutions were evaporated. The residue was dissolved in 100 ml of 10% strength by weight aqueous hydrochloric acid and extracted with 4×100 ml of chloroform. The organic phases were combined, dried and evaporated, giving 6.43 g of (S,S)-1,6-diacetyl-pyrrolopiperidine (38% of theory, purity greater than 95%, m.p. 58 to 60° C.). The aqueous phase was rendered alkaline (pH greater than 10) using 45% strength by weight aqueous sodium hydroxide solution and extracted with 4×100 ml of chloroform. The combined organic phases were dried using sodium sulphate and evaporated, giving 8.2 g of (R,R)-6-acetylpyrrolopiperidine with 96.5% by weight content (=62% of theory, m.p. 83.6 to 84.2° C.).

Example 2

1 g of (S,S)-1,6-diacetyl-pyrrolopiperidine was dissolved in 10 ml of concentrated aqueous hydrochloric acid and refluxed for 24 hours. The mixture was then rendered alkaline using aqueous sodium hydroxide solution and extracted with 3×20 ml of chloroform. The combined organic phases were dried over sodium sulphate and evaporated, giving 0.55 g of (S,S)-pyrrolopiperidine (=95% of theory). Racemization was not observed.

Example 3

1 g of (R,R)-6-acetyl-pyrrolopiperidine was dissolved in 10 ml of concentrated aqueous hydrochloric acid and refluxed for 24 hours. The mixture was then rendered alkaline using aqueous sodium hydroxide solution and extracted with 3×20 ml of chloroform. The combined organic phases were dried over sodium sulphate and evaporated, giving 0.7 g of (R,R)-pyrrolopiperidine (=93% of theory). Racemization was not observed.

Although the present invention has been described in detail with reference to certain preferred versions thereof, other variations are possible. Therefore, the spirit and scope of the appended claims should not be limited to the description of the versions contained therein.

What is claimed is:

1. Method for the racemate resolution of cis- and trans-pyrrolopiperidine, characterized in that a mixture, which comprises (R,R)- and (S,S)-pyrrolopiperidine or (S,R)- and (R,S)-pyrrolopiperidine, is enzymatically monoacylated to give a mixture (I) which comprises (R,R)- and (S,S)-6-acyl-pyrrolopiperidine or (S,R)- and (R,S)-6-acyl-pyrrolopiperidine, this mixture (I) is enzymatically further acylated to give a mixture (II) which comprises (S,S)-1,6-diacyl- and (R,R)-6-acyl-pyrrolipiperidine or (S,R)-1,6-diacyl- and (R,S)-6-acyl-pyrrolopiperidine, the enzyme and optionally solvent and excess acylating agent are separated off from the mixture (II), and the remainder is treated with aqueous acid, and (S,S)-1,6-diacyl-pyrrolopiperidine or (S,R)-1,6-diacyl-pyrrolopiperidine is separated off by extraction, and the extraction residue is rendered alkaline, and (R,R)-6-acyl-pyrrolopiperidine or (R,S)-6-acyl-pyrrolopiperidine is separated off by extraction.

2. Process according to claim 1, characterized in that the acylating agents used are those of the formula (I)

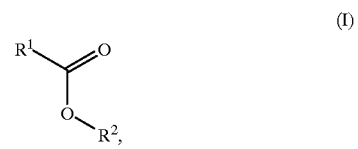

in which

R$^1$ and R$^2$ independently of one another are hydrogen or C$_1$–C$_{12}$-alkyl, and the two acylating reactions are carried out as a one-pot reaction at from 10 to 90° C.

3. Process according to claim 1, wherein the enzyme used is a hydrolase in native or immobilized form.

4. Process according to claim 1, wherein the aqueous acid used is from 2 to 50% strength by weight sulphuric, hydrochloric, phosphoric or acetic acid, in an amount such that the pH following the addition of acid is 4 or less.

5. Process according to claim 1, wherein the extraction residue is rendered alkaline up to a pH of 7.5 or higher using alkali metal hydroxide, alkali metal carbonate, alkali metal hydrogencarbonate, calcium hydroxide or ammonia.

* * * * *